United States Patent [19]

Richter et al.

[11] Patent Number: 4,748,974

[45] Date of Patent: Jun. 7, 1988

[54] LAMINATED DRESSING

[75] Inventors: Roland Richter, Cologne; Wolfram Mayer; Hanns P. Müller, both of Odenthal; Dietmar Schäpel, Cologne; Dietmar Strache, Alfeld, all of Fed. Rep. of Germany

[73] Assignee: Bayer Aktiengesellschaft, Leverkusen, Fed. Rep. of Germany

[21] Appl. No.: 15,404

[22] Filed: Feb. 17, 1987

[30] Foreign Application Priority Data

Feb. 19, 1986 [DE] Fed. Rep. of Germany ....... 3605198

[51] Int. Cl.$^4$ ............................................. A61F 13/04
[52] U.S. Cl. ..................................... 128/91 R; 128/90
[58] Field of Search ..................................... 128/90, 91

[56] References Cited

U.S. PATENT DOCUMENTS

| | | | |
|---|---|---|---|
| 2,127,552 | 8/1938 | Dahmen | 128/90 |
| 2,697,434 | 12/1954 | Rodman | 128/90 |
| 2,914,421 | 11/1959 | Wiener | 128/91 R |
| 4,376,438 | 3/1983 | Straube et al. | 128/90 |
| 4,411,262 | 10/1983 | von Bonin et al. | 128/90 |
| 4,502,479 | 3/1985 | Garwood et al. | 128/90 |
| 4,544,683 | 10/1985 | Muller et al. | 523/111 |
| 4,570,622 | 2/1986 | von Bonin | 128/90 |

FOREIGN PATENT DOCUMENTS 6607  1/1980  European Pat. Off. ............. 128/90

OTHER PUBLICATIONS

Chemical Orthopaedics and Related Research 103, pp. 109–117, 1974.

*Primary Examiner*—Gregory E. McNeil
*Attorney, Agent, or Firm*—Connolly & Hutz

[57] ABSTRACT

A stiff, water resistant laminated medical or veterinary dressing is described along with a procedure for forming the final hardened dressing. The dressing is obtained by treating a gypsum bandage with an aqueous dispersion of a synthetic resin and then forming a layer from it which is immediately adjacent to a layer formed from a water hardenable synthetic resin bandage. Either layer may be formed first and further layers may be formed so long as the layers alternate between those formed from wraps of the gypsum bandages and those formed from wraps of the synthetic resin bandage.

20 Claims, No Drawings

LAMINATED DRESSING

Field of the Invention

The invention relates to laminated dressings for medical or veterinary use.

BACKGROUND OF THE INVENTION

The use of gypsum-impregnated bandages as a stiffening dressing material is known. Such gypsum dressings are undesirably heavy, have a low permeability to air, rapidly lose their strength in the moist state, for example by the action of water on the hardened dressing, impede diagnostic evaluation of X-ray photographs because they absorb and scatter X-rays, and frequently give rise to skin irritation, caused by bacterial or fungal growth in the dressing, because of their retention of water.

Supporting dressings of a synthetic material, in which a textile carrier material or a carrier material based on glass fibres is coated with a polymer, for example a polyurethane which hardens in the presence of water, are also known (Chemical Orthopaedices and Related Research 103, 109–117 (1974), DE-OS (German Published Specification) No. 2,357,931 and U.S. Pat. Nos. 4 4,376,438, 4,411,262, 4,502,479 and 4,570,622). The supporting dressings based on synthetic material can be modelled to lesser degree than can gypsum dressings.

SUMMARY OF THE INVENTION

Laminated dressings have been found which contain, in separate layers and each on a carrier material, gypsum and a synthetic resin which is hardened by water, at least the gypsum layers being finished with a synthetic dispersion.

The laminated dressings according to the invention can be modelled to a high degree, as well as having a high stability to fracture.

DETAILED DESCRIPTION OF THE INVENTION

Gypsum for the laminated dressings according to the invention can be dehydrated (for example the anhydride) or completely or partly hydrated calcium sulphate, which can also contain activities for processing to gypsum bandages of the support material.

The additives should, for example, improve the adhesion to the textile carrier and increase the resistance of the hardened gypsum to water. The additives are in general incorporated together with the calcium sulphate during the production of the gypsum bandages.

Additives can be, for example, inorganic salts, such as diatemaceous earth, chalk, aluminosilicales and kaolins, or organic plastics, such as alkylaryl sulphonates, ligninsulphonic acid salts, melamine resins or cellulose ethers and starch ethers (Ullmann 1976, Volume 12, page 306).

The gypsum bandages mentioned are known per se.

Synthetic resins which harden in water are preferably resin based on polyurethane and polyvinyl resin.

Possible polyurethanes which harden in water are, according to the invention, all the organic polyisocyanates which are known per se, that is to say any desired compounds or mixtures of compounds which contain at least two organically bonded isocyanate groups per molecule. These include both low molecular weight polyisocyanates with a molecular weight of below 400 and modification products of such low molecular polyisocyanates with a molecular weight, which can be calculated from the functionality and the content of functional groups, of, for example, 400 to 10,000, preferably 600 to 8,000 and in particular 800 to 5,000. Suitable low molecular weight polyisocyanates are, for example, those of the formula $$Q(NOC)_n$$

in which n=2 to 4, preferably 2 to 3, and

Q denotes an aliphatic hydrocarbon radical with 2 to 18, preferably 6 to 10, C atoms, a cycloaliphatic hydrocarbon radical with 4 to 15, preferably 5 to 10, C atoms, an aromatic hydrocarbon radical with 6 to 15, preferably 6 to 13, C atoms or an araliphatic hydrocarbon radical with 8 to 15, preferably 8 to 13, C atoms.

Suitable low molecular polyisocyanates of this type are, for example, hexamethylene diisocyanate, 1,12-dodecane diisocyanate, cyclobutane 1,3-diisocyanate, cyclohexane 1,3- and 1,4-diisocyanate and any desired mixtures of these isomers, 1-isocyanato-3,3,5-trimethyl-5-isocyanatomethylcyclohexane, 2,4- and 2,6-hexahydrotoluylene diisocyanate and any desired mixtures of these isomers, hexahydro-1,3- and/or -1,4-phenylene diisocyanate, perhydro-2,4'- and/or -4,4'-diphenylmethane diisocyanate, 1,3- and 1,4-phenylene diisocyanate, 2,4- and 2,6-toluylene diisocyanate and any desired mixtures of these isomers, diphenylmethane 2,4'- and/or 4,4'-diisocyanate, naphthylene 1,5-diisocyanate, triphenylmethane 4,4',4"-triisocyanate or polyphenyl-polymethylene polyisocyanates, such as are obtained by aniline/formaldehyde condensation and subsequent phosgenation.

Suitable higher molecular weight polyisocyanates are modification products of such simple polyisocyanates, that is to say polyisocyanates with, for example, isocyanurate, carbodiimide, allophanate, biuret or uretdione structural units, such as can be prepared by processes which are known per se from the prior art from the simple polyisocyanates of the abovementioned general formula listed by way of example. Of the higher molecular weight modified polyisocyanates, the prepolymers known from polyurethane chemistry with terminal isocyanate groups in the molecular weight range from 400 to 10,000, preferably 600 to 8,000 and in particular 800 to 5,000, are of particular interest. These compounds are prepared in a manner which is known per se by reaction of excess amounts of simple polyisocyanates of the type mentioned by way of example with organic compounds with at least two groups which are reactive towards isocyanate groups, in particular organic polyhydroxy compounds. Suitable polyhydroxy compounds of this type are both simple polyhydric alcohols, such as, for example, ethylene glycol, trimethylolpropane, propane-1,2-diol or butane-1,2-diol, and in particular higher molecular weight polyether-polyols and/or polyester-polyols of the type known per se from polyurethane chemistry with molecular weights of 600 to 8,000, preferably 800 to 4,000, and with at least two, as a rule 2 to 8 but preferably 2 to 4, primary and/or secondary hydroxyl groups. It is of course also possible to use those NCO-prepolymers which have been obtained, for example, from low molecular weight polyisocyanates of the type mentioned by way of example and less preferred compounds with groups which are reactive towards isocyanate groups, such as, for example, polythioether-polyols, polyacetals containing hydroxyl groups, polyhydroxy-polycarbonates, polyesteramides containing hydroxyl groups or copolymers, containing hydroxyl groups, of olefinically unsaturated compounds. Compounds which are suitable for the preparation of the NCO-prepolymers and have groups which are reactive towards isocyanate groups, in particular hydroxyl groups, are, for example, the compounds disclosed by way of example in U.S. Pat. No. 4,218,543, column 7, line 29 to column 9, line 25. In the preparation of the NCO-prepolymers, these compounds with groups which are reactive towards isocyanate groups are reacted with simple polyisocyanates of the type mentioned above by way of example, an NCO/OH equivalent ratio of >1 being maintained. The NCO-prepolymers in general have an NCO content of 2.5 to 30, preferably 6 to 25% by weight. From this it can already be seen that in the context of the present invention, by "NCO-prepolymers" or by "prepolymers with terminal isocyanate groups" there are to be understood both the reaction products as such and their mixtures with excess amounts of unreacted starting polyisocyanates, which are frequently also called "semi-prepolymers".

Polyisocyanate components which are particularly preferred according to the invention are the technical grade polyisocyanates customary in polyurethane chemistry, that is to say hexamethylene diisocyanate, 1-isocyanato-3,3,5-trimethyl-5-isocyanatomethyl-cyclohexane (isophorone diisocyanate, abbreviated to: IPDI), 4,4'-diisocyanatodicyclohexylmethane, 4,4'-diisocyanatodiphenylmethane, mixtures thereof with the corresponding 2,4'- and 2,2'-isomers, polyisocyanate mixtures of the diphenylmethane series, such as can be obtained by phosgenation of aniline/formaldehyde condensates in a manner which is known per se, the modification products of these technical grade polyisocyanates containing biuret or isocyanurate groups, and in particular NCO-prepolymers of the type mentioned based on these technical grade polyisocyanates on the one hand and, on the other hand, the simple polyols and/or polyether-polyols and/or polyester-polyols mentioned by way of example, and any desired mixtures of such polyisocyanates. Isocyanates with aromatically bonded NCO groups are preferred according to the invention. A polyisocyanate component which is particularly preferred according to the invention is partly carbodiimidated diisocyanatodiphenylmethane, which also contains uretonimine groups as a result of addition of monomeric diisocyanate onto the carbodiimide structure.

Polyvinyl resins which harden in water can be, for example, vinyl compounds which consist of a hydrophilic prepolymer with more than one polymerizable vinyl group and in which a solid, insoluble vinyl redox catalyst is embedded, one constituent of which is encapsulated by a water-soluble or water-permeable shell. Such a redox catalyst is, for example, sodium bisulphite/copper(II) sulphate, in which, for example, the copper sulphate is encapsulated with poly-2-hydroxyethyl methacrylate.

Supporting synthetic dressings which are based on a polyvinyl resin which hardens in water are described, for example, in European Patent No. 0,136,021.

Carrier materials for the gypsum and synthetic resin layers for the laminated dressings according to the invention can be the carrier materials customary for supporting dressings.

Possible carrier materials are massive or porous films or foams of natural or synthetic materials (for example polyurethane), and above all flexible sheet-like structures on a textile basis which are permeable to air, preferably with a weight per unit area of 20 to 1,000 g/m², in particular 30 to 500 g/m². Examples of sheet-like structures which may be mentioned are:

1. Textile woven fabric, knitted fabric or mesh fabric with a weight per unit area of 20 to 200 g/m², preferably 40 to 100 g/m², with a thread count of preferably 2 to 20 threads per running centimetre in the longitudinal and transverse direction. The textile woven fabric or knitted fabric can be produced from any desired natural or synthetic yarns. However, woven fabrics or knitted fabrics which have been produced from cotton yarns, or mixed yarns which in turn have been obtained both from hydrophobic threads or fibres with a relatively high E modulus (for example polyester) and hydrophilic natural or synthetic threads or fibres (for example cotton or polyamide) are preferably used.

2. Glass fibre woven fabrics, knitted fabrics or mesh fabrics with a weight per unit area of 60 to 500 g/m², preferably 100 to 400 g/m², produced from glass fibre yarns with a E modulus of 7,000 to 9,000 (daN/mm²) and a thread count of 3 to 10, preferably 5 to 7, in the longitudinal direction, and with a thread count of 3 to 10, preferably 4 to 6, in the transverse direction, per centimeter of glass fibre fabric are preferred. Those which have a longitudinal stretchability of 10 to 30% are especially preferred. The fabric can be either sized or unsized.

3. Non-bonded or bonded or needled non-woven fabrics based on inorganic and, preferably, organic fibres with a weight per unit area of 30 to 400 g/m², preferably 50 to 200 g/m².

Non-woven fabrics with weights per unit area of up to 1,000 g/m² are also possible for the preparation of stiffening dressings according to the invention in the form of shells or splints. Carrier materials which are suitable according to the invention are also described, for example, in U.S. Pat. Nos. 4,134,397, 3,686,725, 3,882,857, DE-OS (German Published Specification) No. 3,211,634 and European Patent No. A-61,642.

Synthetic dispersions for the laminated dressing according to the invention are in general polyurethanes and/or polyurethaneureas which have a content of chemically incorporated hydrophilic groups which guarantees dispersibility in water.

The hydrophilic groups can be present in the form of (a) ionic groups and/or (b) groups which can be converted into ionic groups by a neutralization reaction and/or (c) ethylene oxide units ($-CH_2-CH_2-O-$) within polyether chains incorporated into the polyurethane(urea) molecule.

All the aqueous polyurethane(urea) dispersions which are known per se and form non-tacky films on drying and which—if appropriate as a result of a content of alcohols and if appropriate other organic solvents—are largely insensitive towards coagulation by electrolytes can be used for the preparation of the synthetic dispersions.

A number of processes are known for the preparation of polyurethane(urea) dispersions in water. A comprehensive presentation is to be found in Angw. Makr. Chem. 26, 85 to 106 (1972), Angw. Chem. 82, 53 to 63 (1970), J. Oil Col. Chem. Assoc. 1970, 53, 363 to 379, Angw. Mak. Chem. 78, 133 to 158, (1981) and in "Chemie und Technologie makromolekularer Stoffe"

(Chemistry and Technology of Macromolecular substances) (29th publication of the Aachen Technical College for the 9th colloquium on 8th May 1981 at the Aachen TC, Specialist Field Chemical Engineering).

A preparation process for aqueous polyurethane (urea) dispersions which is preferred in practice comprises reacting an isocyanate prepolymer, dissolved in an organic solvent, with a chain lengthening agent. Either the prepolymer or the chain lengthening agent thereby contain groups which are ionic or capable of ion formation. Groups capable of ion formation are converted into ionic groups in the course of the polyaddition reaction or thereafter. At the same time or also subsequently, the aqueous dispersions are formed by addition of water and distillated of the organic sovent. As already mentioned, both cationic as well as anionic and non-ionic polyurethane dispersions can be used in the process according to the invention. Preferably, those aqueous polyurethane(urea) dispersions which give polyurethane films with elastic properties on drying up are used. By these there are to be understood, in particular, polyurethanes or polyureas or polyhydrazodicarboxamides which are elastomeric or at least have a notched impact strength and have a ball indentation hardness of less than 1,400 kp/cm$^2$ (60 seconds in accordance with DIN 53,456), and preferably a Shore D hardness of less than 98.

Other synthetic dispersions which are suitable according to the invention are, on the other hand, the aqueous dispersions based on polyvinyl acetate which are used in civil engineering. Examples which may be mentioned are ethylene/vinyl acetate copolymers and vinyl laurate/vinyl acetate copolymers (Plaste und Kautschuk, 17, 162 (1970).

Preferred synthetic dispersions for the laminated dressings according to the invention are stable towards calcium ions and/or sulphate ions. Particularly preferred synthetic dispersions for the laminated dressings according to the invention are water-dispersible polyurethanes with an essentially linear molecular structure, characterized by
(a) terminal polyalkylene oxide-polyether chains with a content of ethylene oxide units of 0.5 to 10% by weight, based on the total polyurethane, and
(b) a content of $=N^{\oplus}=$, $=S^{\oplus}=$, $-COO^{\ominus}$ or $-SO_3^{\ominus}$ groups of 0.1 to 15 milliequivalents per 100 g.

The laminated dressings according to the invention consist of at least one gypsum layer and one synthetic resin layer, the outer layer preferably being a gypsum layer.

The laminated dressings according to the invention in general consist of 2 to 7, preferably 3 to 5, gypsum and synthetic resin layers in alternation.

In the laminated dressings according to the invention, at least the bandages used to form the gypsum layers have been finished with a synthetic dispersion. In the context of the present invention, however, it is also possible to impregnate both the bandages forming the gypsum layers and the bandages forming the layers of plastic with the aqueous synthetic dispersion.

The impregnation level of dispersion solids is in general 1 to 10% by weight, preferably 2 to 5% by weight, based on the particular layer.

A process has also been found for the production of the laminated dressings according to the invention which consists of separate layers of gypsum and synthetic resin, each applied to a carrier material, which is characterized in that at least the gypsum layers used and, if appropriate, the synthetic resin layers are treated with an aqueous dispersion of plastic and the gypsum layers and synthetic resin layers are then applied on top of one another in alternation.

The laminated dressings according to the invention can be produced, for example, as follows:

The gypsum layers on the carrier material (gypsum bandages) are immersed in the aqueous synthetic dispersions and are then immediately wound in the moist state, without further pressing out, over the body to be supported, which has first been covered, if appropriate, with a base material such as a stockinette padding. When one gypsum layer has been applied, the synthetic resin layer (synthetic bandages) is applied to the moist gypsum. This synthetic bandage is, however, first immersed in water and, if appropriate, impregnated with the aqueous synthetic dispersion.

It is possible for the aqueous synthetic dispersion to contain other water-soluble organic solvents, such as alcohols (for example methanol or ethanol) or acetone, in amounts of 1 to 20% by weight, preferably 2 to 10% by weight.

The gypsum bandages and optionally the synthetic resin bandages are saturated with the synthetic dispersion. Adequate saturation is in general achieved by immersion for 2 to 10 seconds.

It is essential for the present invention that the bandages of gypsum contain aqueous synthetic dispersion, when hardened.

According to the invention, 2 to 7 layers of gypsum and synthetic resin, in each case on a carrier material, at least the gypsum layers being finished with an aqueous synthetic dispersion, can be used to produce laminated dressings.

It is to be described as exceptionally surprising that, in contrast to the gypsum dressings which are impregnated with aqueous polyurethane(urea) dispersions and are described in European Patent No. 128,399, the laminated dressings according to the invention harden rapidly and readily release excess water.

The laminated dressings according to the invention are distinguished by an excellent resistance to water, but without the transportation of water being prevented, a high elasticity and a high stability to fracture. It is remarkable that breaking out and crumbling of the edges is absent in the laminated dressings according to the invention. In comparison with non-finished laminated dressings, the adhesion between the individual layers of the laminate is very high.

The laminated dressings according to the invention are particularly suitable for supporting dressings for immobilization of parts of the human or animal body.

EXAMPLES

The following components are used in the examples below: 1. Gypsum bandages:

Commercially available gypsum bandages (Biplatrix ® from Beiersdorf of the Federal Republic of Germany), in which 500 to 600 g/m$^2$ of the gypsum are applied to a carrier of cotton knitted fabric, are used.

2. Synthetic resin bandages

Commerically available synthetic resin bandages in which a textile knitted fabric of cotton with a weight per unit area of 60±10 g/m$^2$ is coated with 150±20% by weight of a polyurethane which contains aromatic isocyanate groups and has an NCO content of 18±2% by weight and a viscosity (25° C.) of 10,000–25,000 mPas (Deltacast ® from Johnson +Johnson GmbH of the Federal Republic of Germany).

3. Synthetic dispersion (a) Polyurethane dispersion (PU dispersion)

The PU dispersion used below can be prepared as follows: 1,632 parts of a polyester-diol of hexane-1,6-diol, 2,2-dimethylpropane-1,3-diol and adipic acid with an OH number of 63 is dehydrated at 100° C. under a vacuum of about 14 mm Hg and, after addition of 85 parts of a polyether-monoalcohol of n-butanol, ethylene oxide and propylene oxide (in a molar ratio of 83:17) with an OH number of 30 (1), a mixture of 244.2 parts of 3-isocyanatomethyl-3,5,5-trimethylhexyl isocyanate and 185 parts of hexane 1,6-diisocyanate is added. The mixture is stirred at 100° C. until it has an NCO content of 4.6% by weight. After cooling to 50°-60° C., 3,200 parts of anhydrous acetone are added. A mixture of 107 parts of sodium (2-aminoethyl)-2-aminoethanesulphonate and 10 parts of hydrazine monohydrate, dissolved in 260 parts of water, is slowly stirred into this acetone solution. After the mixture has been subsequently stirred for 10 minutes, 2,280 parts of water are slowly added, with vigorous stirring. A bluish-white dispersion of the solid in a mixture of water and acetone is thereby formed. After removal of the acetone by distillation, an aqueous dispersion of the solid with a concentration of 50% remains. Measurement of the particle diameter with the aid of light scattering gives a value of 200±20 nm.

The solid in the dispersion contains 3.1% of polyethylene oxide segments and 3 mequivalent of sulphonate groups ($-SO_3^{\ominus}$) per 100 g of solid. (b) Polyvinyl resin dispersion (EVA dispersion)

A commercially available aqueous dispersion of a copolymer of vinyl acetate and ethylene; pH=4; particle size 0.5 to 1 μm, strength 53%, viscosity 8000 mpas/sec (Vinnapas ® dispersion LT 441 from Wacker Chemie GmbH, of the Federal Republic of Germany, company publication No. 3710,283).

EXAMPLE 1

(Production of finished gypsum bandages)

14 gypsum bandages 8 cm×400 cm in size (dry weight about 170 g) were each immersed in succession 4 to 5 times in 1,900 g of a 5% strength by weight PU dispersion until no further air bubbles rise. The bandages are now squeezed out only gently and are removed and then processed to the corresponding test pieces of the following examples. The dispersion which remains is investigated: Amount: 780 g, solids content: 5.65% by weight.

This means that after treatment with the aqueous PU dispersion, the 14 gypsum bandages have taken up 51 g of the solids content of the synthetic dispersion, corresponding to a degree of impregnation of 2.3%.

EXAMPLE 2

The following test piece was wound:
Internal diameter: 87 mm
Width: 90 mm.
Test piece A:
1st layer: A gypsum bandage 10 cm×300 cm in size was immersed in water for 5 seconds and wound three times around a corresponding spool (diameter: 87 mm).
2nd layer: A synthetic resin bandage 10 cm×300 cm in size was immersed in water for 5 seconds, with squeezing out, and wound twice around the gypsum layer present.
3rd layer: Another gypsum bandage 10 cm×300 cm in size was immersed in water for 5 seconds and wound three times around the synthetic resin bandage present. After hardening and removal of the spool, a shaped article which has a breaking strength of 15.5 N/cm in the radial direction was obtained. (Determined with a machine from Zwick, No. 1484, test piece between plates, maximum value at an advance of 25 mm/min).

Test piece B:
1st layer as for A, but with 10% strength by weight EVA dispersion instead of water.
2nd layer as for A.
3rd layer as for A, but with 10% strength by weight EVA dispersion instead of water.
Breaking strength: 19.1 N/cm (determination as for A).

Test piece C:
1st layer as for A, but with 10% strength by weight PU dispersion instead of water.
2nd layer as for A.
3rd layer as for A, but with 10% strength by weight PU dispersion instead of water.
Breaking strength: 19.2 N/cm (determination as for A).

EXAMPLE 3

The following test pieces were wound:
Internal diameter: 100 mm
Width: 90 mm
Test piece A:
1st layer: A gypsum dressing 8 cm×400 cm in size was immersed in water for 5 seconds and wound three times round a corresponding spool (diameter: 10 cm).
2nd layer: A synthetic resin bandage 7.5 cm×300 cm in size was immersed in water for 5 seconds, with squeezing out, and wound twice round the gypsum layer.
3rd layer: A gypsum bandage 8 cm×400 cm in size was immersed in water for 5 seconds and wound three times round the synthetic resin bandage present.
After hardening and removal of the spool, a shaped article which has a breaking strength of 12.2 N/cm in the radial direction was obtained. (Determination with a machine from Zwick, No. 1484, test piece between plates, maximum value at an advance of 25 mm/minute.)

Test piece B:
1st layer as for A, but with a 5% strength by weight PU dispersion instead of water.
2nd layer as for A.
3rd layer as for A, but with a 5% strength by weight PU dispersion instead of water.
Breaking strength: 13.6 N/cm (determination as for A).

Test piece C:
1st layer as for B,
2nd layer as for A, but also with a 5% strength by weight PU dispersion instead of water.
3rd layer as for B.
Breaking strength: 14.6 N/cm (determination as for A).

EXAMPLE 4

The following test pieces were wound:
Internal diameter: 100 mm
Width: 200 mm

Test piece A: as for test piece A, Example 3, but using a gypsum bandage 10 cm×300 cm in size Test piece B: as for test piece B, Example 3, but using a gypsum bandage 10 cm×300 cm in size.

The maximum load (fracture or delamination) in the direction of the longitudinal axis (=standing) was determined on the test pieces:

Test piece A: 12 kp
Test piece B: 20 kp.

EXAMPLE 5

The following test pieces were wound:
Internal diameter: 87 mm
Width: 100 mm

Test piece A:

1st layer: A synthetic resin bandage 10 cm×300 cm in size was immersed in water for 5 seconds, with squeezing out, and wound three times round a corresponding spool (diameter 87 mm).

2nd layer: A gypsum bandage 10 cm×200 cm in size (level of coating: 510±20 g/m² of gypsum) was immersed in water for 5 seconds and wound four times round the synthetic resin layer present.

Test piece B:

1st layer: as for A, but with 5% strength by weight PU dispersion instead of water 2nd layer: as for A, but with 5% strength by weight PU dispersion instead of water After hardening and removal of the spool, in each case a shaped article which has a breaking strength of 11.4 N/cm in the case of A and
12.4 N/cm in the case of B in its radial direction was obtained. (Determination with a machine from Zwick, No. 1484; test piece between plates, maximum value at an advance of 25 mm/minute.)

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A stiff, water resistant laminated medical or veterinary dressing comprising at least one layer formed from the wraps of a gypsum bandage immediately adjacent to a layer formed from the wraps of a water hardenable synthetic resin bandage wherein at least the gypsum bandage was immersed in an aqueous dispersion of a synthetic resin for a period sufficient for the absorption of some of the dispersion solids into the gypsum before the gypsum bandage was allowed to cure.

2. A process for forming a water resistant, stiff laminated medical or veterinary dressing comprising
   (a) immersing an uncured gypsum bandage in an aqueous dispersion of a synthetic resin for a period sufficient for the absorption of some of the dispersion solids into the gypsum,
   (b) forming a layer from the wraps of the gypsum bandage which is immediately adjacent to a layer formed from the wraps of a water hardenable synthetic resin bandage by either forming the gypsum bandage layer over an uncured synthetic resin bandage layer or forming the synthetic resin bandage layer over the uncured gypsum bandage layer, and
   (c) allowing the laminated layers to cure to final hardness by interaction with water.

3. The laminated dressing of claim 1 wherein the water hardenable synthetic resin is either a polyvinyl resin or a polyurethane resin.

4. The laminated dressing of claim 1 or 3 in which the aqueous dispersion is stable towards calcium ions and is a dispersion of either a polyurethane or a polyvinyl acetate.

5. The laminated dressing of claim 4 wherein the synthetic resin bandage and the gypsum bandage utilize a carrier material selected from the group consisting of woven or knitted cotton fibers, synthetic textile fibers, glass fibers and combinations thereof.

6. The laminated dressing of claim 5 wherein the outermost layer is formed from a gypsum bandage.

7. The laminated dressing of claim 1 or 3 wherein there are between 2 and 7 alternating layers formed from gypsum and water hardenable synthetic resin bandages.

8. The laminated dressing of claim 7 wherein the outermost layer is formed from a gypsum bandage.

9. The laminated dressing of claim 1 or 3 wherein the gypsum of each gypsum layer has absorbed between about 1 and 10 weight percent, based on the weight of the layer, of the dispersion solids.

10. The laminated dressing of claim 1 or 3 wherein the water hardenable synthetic resin bandages have also been immersed in the aqueous dispersion for a period sufficient for the absorption of some of the dispersion solids.

11. The laminated dressing of claim 10 wherein
    (a) the water hardenable synthetic resin is either a polyvinyl resin or a polyurethane resin,
    (b) the aqueous dispersion is stable to calcium ions and is a dispersion of either a polyurethane resin or a polyvinyl acetate resin,
    (c) the carrier material for the synthetic resin bandage and the gypsum bandage is selected from the group consisting of woven or knitted cotton fibers, synthetic textile fibers, glass fibers and combinations thereof,
    (d) each layer has absorbed between about 1 and 10 weight percent, based on the weight of the layer, of dispersion solids, and
    (e) there are between 2 and 7 alternating layers formed from the gypsum and water hardenable synthetic resin bandages.

12. The laminated dressing of claim 11 wherein the outermost layer is formed from a gypsum bandage.

13. The process of claim 2 wherein the aqueous dispersion has a solids concentration of between 1 and 50 weight percent.

14. The process of claim 13 wherein the aqueous dispersion has a solids concentration of between about 3 and 30 weight percent.

15. The process of claim 2 or 14 wherein
    (a) the water hardenable synthetic resin is either a polyvinyl resin or a polyurethane resin,
    (b) the aqueous dispersion is stable to calcium ions and is a dispersion of either a polyurethane resin or a polyvinyl acetate resin,
    (c) the synthetic resin bandages and the gypsum bandages utilize a carrier material selected from the group consisting of woven or knitted cotton fibers, synthetic textile fibers, glass fibers and combinations thereof,
    (d) the immersion of each bandage is of sufficient duration that it absorbs between about 1 and 10 weight percent, based on the weight of the bandage, of dispersion solids, and (e) between 2 and 7 alternating layers are formed from the gypsum bandages and the water hardenable synthetic resin bandages.

16. The process of claim 15 wherein the outermost layer is formed from a gypsum bandage.

17. The process of claim 15 wherein the water hardenable synthetic resin is a polyurethane.

18. The process of claim 17 wherein the aqueously dispersed resin is a polyurethane.

19. A stiff, water resistant laminated medical or veterinary dressing comprising at least one layer formed from the wraps of a gypsum bandage immediately adjacent to a layer formed from the wraps of a water hardenable, polyurethane bandage wherein at least the gypsum bandage was immersed in an aqueous dispersion of either a polyvinyl acetate or a polyurethane which is stable to calcium ions for a period sufficient to absorb between 1 and 10 weight percent, based on the weight of the bandage, of dispersion solids before the gypsum bandage was allowed to cure.

20. A process for forming a stiff, water resistant laminated medical or veterinary dressing comprising (a) immersing an uncured gypsum bandage in an aqueous dispersion of between about 1 and 50 weight percent of a polyvinyl acetate or polyurethane resin which is stable to calcium ions for a period sufficient for the absorption of between about 1 and 10 weight percent, based on the weight of the bandage, of dispersion solids, (b) forming a layer from the wraps of the gypsum bandage which is immediately adjacent to a layer formed from the wraps of a water hardenable polyurethane bandage by either forming the gypsum layer over an uncured polyurethane bandage layer or forming the polyurethane bandage layer over the uncured gypsum bandage layer, and (c) allowing the laminated layers to cure to final hardness by interaction with water.

* * * * *